Dec. 16, 1947. W. A. HOYNE Plant Pat. 771
CARNATION PLANT
Filed Dec. 19, 1946
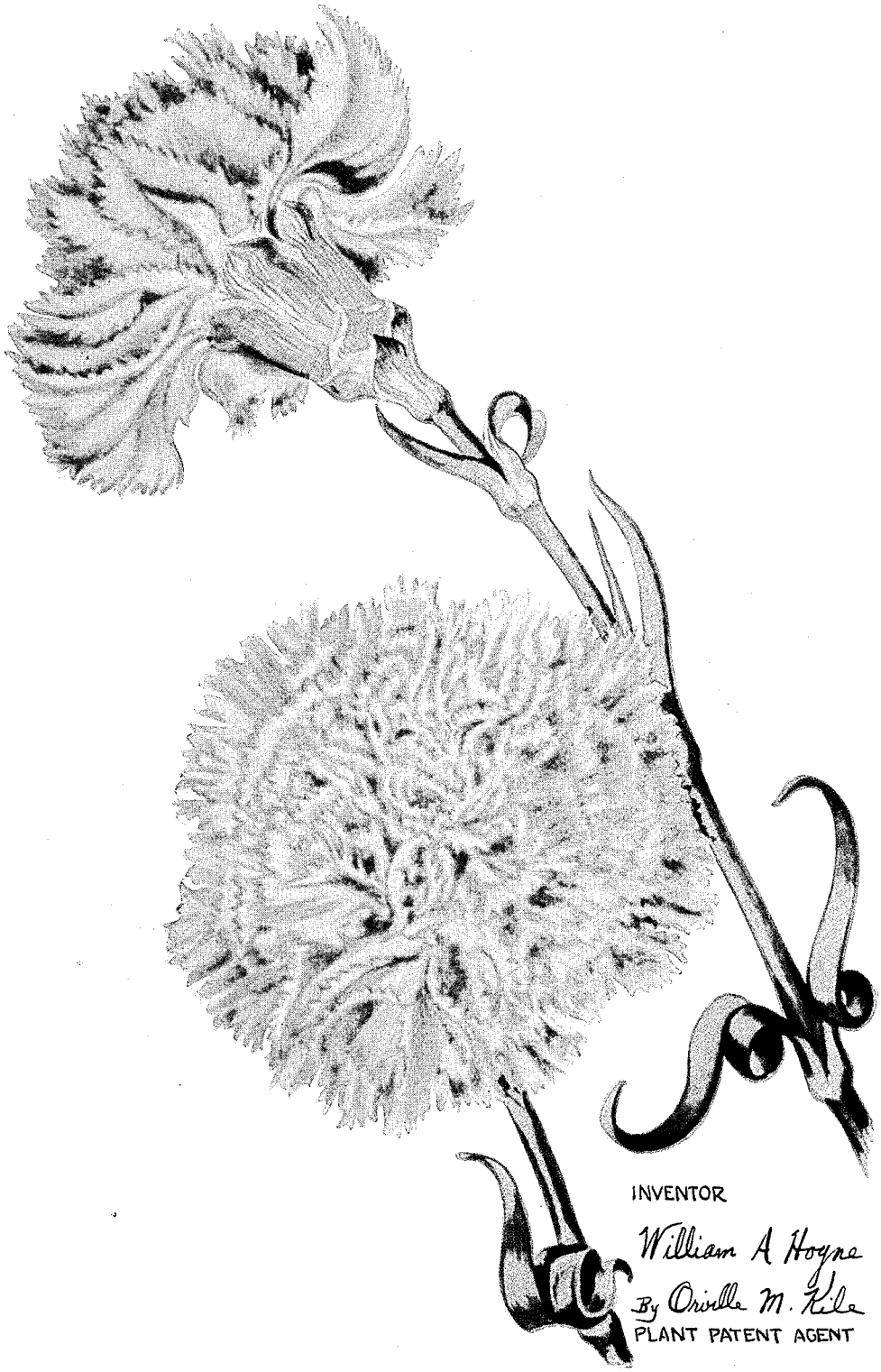
INVENTOR
William A Hoyne
By Orville M. Kile
PLANT PATENT AGENT Patented Dec. 16, 1947

Plant Pat. 771

UNITED STATES PATENT OFFICE

771

CARNATION PLANT

William A. Hoyne, Colorado Springs, Colo., assignor to Broadmoor Hotel, Inc., Colorado Springs, Colo., a corporation of Colorado Application December 19, 1946, Serial No. 717,203

1 Claim. (Cl. 47—60)

My present invention relates to an improved variety of carnation plant of the large-flowered greenhouse type. This new variety originated as a seedling resulting from a cross between King Cardinal (Plant Patent No. 148) and Gardenia.

The combination of good qualities makes this an outstanding and desirable variety for general use. The plant is very healthy and a prolific producer. The flowers are of high quality, good form and color, and last a very long time without fading. Stem, foliage and calyx are strong and durable.

The variety has been produced asexually from cuttings through several generations and its distinguishing qualities have proved to be firmly fixed.

Accompanying illustrations show in approximately true colors a full front view of a typical specimen of the flower of this new variety and a back view indicating the structure of the calyx. Portions of the stems and foilage are also shown.

Following is a detailed description of the plant and flower of this new variety. Color plate references indicate Ridgway's Color Standards and Nomenclature.

*The plant*

Growth habit: Vigorous and upright; usual height 30 to 36 inches. Has strong shoots from base of plant and no "grassy" growth. Cuttings root very easily, even in warm weather.

Disease resistance: Very resistant to usual diseases affecting carnations. No diseases have ever been found on plants of this variety.

Flowering habit: Continuous bloomer. Very prolific producer of large flowers throughout the season. Disbuds (extra buds which must be removed) are seldom present in this variety. There are never more than two buds on the stem and these usually come at the top next to the flowering bud. This is a rare feature in carnations since most other varieties must be heavily disbudded to produce quality flowers.

Foliage: Average quantity but the lower leaves are large in size. Lower leaves are approximately ⅜ inch wide and up to 6 inches long; dark green, covered with a gray bloom—the total color effect being approximately Varley's Green (Plate XVIII). Although some leaves curl slightly, the general effect is non-curling. Substance of the leaves is heavy and wax-like.

Stems: Lighter than the foliage in color, being approximately Civette Green (Plate XVIII). An important feature of the variety is its very strong, stiff stems which stand upright without bending.

*The flower*

Bud:

*Shape.*—Bulged but tapering.

*Color.*—Scarlet Red (Plate I) or slightly darker.

*Size.*—1 to 1½ inches in diameter as color begins to show.

*Opening.*—Speed of opening is moderate.

Flower:

*Size.*—Large, measuring 4 to 5 inches in diameter in cool weather but somewhat smaller in hot weather.

*Form.*—The flower of this variety has a unique form in that it usually has three distinctly discernible rosettes of petals in the center. The flower is very full-petaled, the outer petals being much larger and showing separately. The inner petals are shorter and stand up straight.

*Color.*—Individual petals are Scarlet Red (Plate I) in their center, shading darker at the edges. The general color effect of the flower might be called Dark Scarlet Red, although such color is not shown in Ridgway's.

*Petalage.*—Average petalage in the month of July is about 72, including all small petals.

*Calyx.*—Very tough and non-splitting. Lighter in color than stems, being near Rinneman's Green (Plate XVIII) although a little brighter. Very wide, being approximately 1 inch in width at top in its natural position or 1¼ inches when flattened. The strength and width of the calyx are important in a carnation having such a large petalage.

*Petals.*—Irregularly fringed and scalloped but not deeply cut. Outer petals are up to 1½ inches in width.

*Fragrance.*—Moderate.

*Longevity.*—Lasting quality as a cut flower is excellent, since they frequently last 15 days or more after being cut. Flowers do not fade, bleach or change color and do not "go to sleep" at night or in shipping.

Reproductive organs:

*Ovary.*—Very large. Contains many ovules. Set high on pithy pedestal.

*Pistils.*—Large, approximately 1½ inches long. Usually 3-pronged White at base and tipped with pink. Tips curled. Slightly visible in open flower although curled so that they do not protrude beyond the petals.

*Stamens.*—Few. Straggling. Creamy white.

*Comparison*

The variety most like my new variety is the subject of Plant Patent No. 669, but there are a number of differences, principally as follows.

1. My new variety has a different form of flower—the center of mine being swirled usually in three rosettes and with petals shorter and smaller, while No. 669 is practically the same length all over and without swirls.

2. Petalage of my new variety is considerably greater.

3. Foliage on my new variety is longer.

4. Calyx of my flower is broader.

5. Plants of my variety do not grow quite so tall but remain more upright.

6. My variety has different parentage.

7. My variety requires much less disbudding to produce choice flowers.

8. My variety reproduces from cuttings with greater ease.

9. Under same conditions the flower of my variety last longer when cut.

Having thus disclosed my invention, I claim:

The new and distinct variety of carnation plant, substantially as herein shown and described, characterized particularly by its disease-resistant and vigorous growth; its prolific and continuous production of good quality flowers; the absence of superfluous buds; the ease with which its cuttings root; its strong, stiff, upright stems; its broad non-splitting calyx; and its large, dark scarlet red flowers which have a swirled formation, do not fade, and last a very long time.

WILLIAM A. HOYNE.